(12) United States Patent
Beerman et al.

(10) Patent No.: US 7,851,450 B2
(45) Date of Patent: Dec. 14, 2010

(54) GANGLIOSIDES WITH A MODIFIED ACYL FUNCTION

(75) Inventors: Christopher Beerman, Neu-Anspach (DE); Lars Bode, Giessen (DE); Gunther Boehm, Echzell (DE)

(73) Assignee: N.V. Nutricia, Zoetermeer (NL)

( * ) Notice: Subject to any disclaimer, the term of this patent is extended or adjusted under 35 U.S.C. 154(b) by 1515 days.

(21) Appl. No.: 10/497,173

(22) PCT Filed: May 27, 2003

(86) PCT No.: PCT/EP03/05611

§ 371 (c)(1),
(2), (4) Date: Jun. 9, 2004

(87) PCT Pub. No.: WO03/106474

PCT Pub. Date: Dec. 24, 2003

(65) Prior Publication Data

US 2005/0075310 A1    Apr. 7, 2005

(30) Foreign Application Priority Data

Jun. 13, 2002 (DE) ................................ 102 26 367

(51) Int. Cl.
A61K 31/702 (2006.01)
A61K 31/7028 (2006.01)
A61K 31/7032 (2006.01)
C07H 15/04 (2006.01)
C07H 15/10 (2006.01)

(52) U.S. Cl. .................................. 514/24; 536/17.9

(58) Field of Classification Search ............... 514/25, 514/54, 558, 61; 435/375, 232; 536/53, 536/17.9, 18.6, 141, 55.1, 23.1, 24.5, 25, 536/123; 424/450; 558/169, 175; 562/564
See application file for complete search history.

(56) References Cited

U.S. PATENT DOCUMENTS 5,366,963 A * 11/1994 Ladisch .................... 514/54
5,567,684 A * 10/1996 Ladisch et al. ............. 514/25
5,885,632 A *  3/1999 Takebe et al. .............. 426/46
6,992,068 B2 *  1/2006 Yoshida et al. ............. 514/26

FOREIGN PATENT DOCUMENTS

DE    44 30 041 A    2/1996
JP    05279379    * 10/1993

OTHER PUBLICATIONS

Heitmann et al. "Modulation of CD4 expression on helper T lymphocytes and U937 cells by ganglioside GM3 and its derivatives." New Developments and New Applications in Animal Cell Technology, 601-605, 1998, Kluwer Academic Publishers.*
Ladisch et al., "Aberrant Fatty Acyl alpha-hydroxylation in Human Neuroblastoma Tumor Gangliosides" Journal of Biological Chemistry (1989) vol. 264 No. 20, pp. 12097-12105.*
Chen S. et al., "Quantitative analysis of the molecular species of monosialogangliosides by continuous-flow fast-atom bombardment mass spectrometry", Rapid Communications in Mass Spectrometry, Heyden, London, GB, Bd. 5, Nr. 12, Dec. 1991, pp. 618-621, XP009018753.
M.C. Sullards et al., "Structure determination of soybean and wheat glucosylceramides by tandem mass spectrometry", J. Mass Spectrom, Bd. 35, 2000, pp. 347-353, XP008024413.
D. Heitmann et al., "Modulation of CD4 expression on helper T lymphocytes and U937 cells by ganglioside GM3 and its derivatives", New Developments and New Applications in Animal Cell Technology, 1998, pp. 601-605, XP008024421.
Masahiro Morita et al., "Structure-Activity Relationship of Alpha-Galactosylceramides Against B16-Bearing Mice", Journal of Medicinal Chemistry, American Chemical Society, Washington, US, Bd. 38, 1995, pp. 2176-2187, XP002919134.
S. Sonnino et al., "Preparation of GMI ganglioside molecular species having homogeneous fatty acid and long chain base moieties", J. Lipid Res., Bd. 26, 1985, pp. 248-257, XP002261710.

* cited by examiner

*Primary Examiner*—Eric S Olson
(74) *Attorney, Agent, or Firm*—Bacon & Thomas PLLC

(57) ABSTRACT

The invention relates to a ganglioside mixture, consisting of gangliosides, of the following general formula: (sugar)-$OCH_2$—$CH(-NH-CO-R^1)$—$CH(OH)$—$CH=CH-R^2$, wherein (sugar) represents a sugar radical, the group —$CO-R^1$ represents an acyl-fatty acid which is bonded to the radical of the molecule in the form of an amide, $R^1$ represents a straight saturated alkyl radical having at least 10 C-atoms and $R^2$ represents a straight, saturated alkyl radical having at least 10 C-atoms or a straight alkenyl radical having at least 10 C-atoms and one, two or three double bond(s). Said mixture is characterised in that at least 10 wt. % of the gangliosides of the general formula I are of the group —$CO-R^1$ and the acyl-fatty acids are a C20:0 fatty acid. Said mixtures exhibit an improved biological activity.

22 Claims, No Drawings

GANGLIOSIDES WITH A MODIFIED ACYL FUNCTION

The invention relates to a ganglioside mixture, the use of this ganglioside mixture for preparing a dietetic, pharmaceutical and food composition, as well as a corresponding composition.

Gangliosides are glycolipids of a complicated structure, which are predominantly located on the outer surface of the plasma membrane of a cell. They contain a polar part (head) made up of sugars and sugar derivatives and, in some cases, N-acetyl neuraminic acid, as well as several nonpolar aliphatic chains made up of fatty acids and their derivatives.

The structure of the ganglioside oligosaccharide chain directly determines the cell-cell interaction (cell adhesions), the receptor coverage (e.g. IL-2, selectines), cf. Robb, R. J., J. Immunol. 1986, 136, 971-976, enterotoxin linkage (antibacterial/antiviral and prebiotic effects), cf. Rueda, R., Sabetel, J. L., Maldonaldo, J., Molinos-Font, J. A., Gil, A. J. Pediatr. 1998, 133, 90-94, adhesion/antibody linkage, cf. Welte, K., Miller, G., Chapman, P. B., Yuasa H., Natoli, E., Kunicka, J. E., Cordon-Cardo, C., Buhrer, C., Old, L. J., Houghton, A. N., J. Immunol. 1987, 139, 1763-1771 and cellular signal transduction (GM3 in the case of T-cells), cf. Rippo, M. R., Malisan, F., Ravagnan, L., Tomassini, B., Condo, I., Constantini, P., Susin, S. A., Rufini, A., Todaro, M., Kroemer, G., Testi, R. FASEB J. 2000, 14, 2047-2057.

The fatty acid composition is however responsible for the spatial arrangement of the molecules within a membrane (micro-domain formation/clustering), and is a co-determinant for the substrate-specific reaction of glycolipids in the metabolism (enzyme-substrate specificity).

When the literature refers to fatty acid compositions in the context of gangliosides, very often no distinction is made between the two nonpolar aliphatic chains, both of which are called fatty acids. These fatty acids, however, are a structure-determining and function-determining element, cf. Ladisch, S., Hasegawa, A.; Li, R., Kiso, M. Biochemistry 1999, 34, 1197-1202. The N-acyl sphingosine portion of gangliosides (ceramide) is of importance as an intracellular signal-mediating molecule. The long-chain acyl groups of gangliosides are omnipresent fatty acids in biological systems, and impart these gangliosides a high bio-activity in their manifold functions.

Gangliosides are enzymatically (lyosomal enzymes) intracellularly converted into ceramide, this is converted into sphingomyelin and then to sphingosine, sphingosine-1P. Ceramide, via sphingomyelin conversion, also influences the synthesis of diacyl glycerol and phosphoryl diacyl glycerol. These substances all are highly potent signal-mediating molecules. Gangliosides and gangliosides converted into ceramide thus determine the metabolism and the cell function in manifold ways. While the 3-keto bound fatty acid of the ganglioside structurally and functionally co-determines all metabolites of the ceramide, e.g. sphingosine, i.e. this aliphatic chain remains unchanged in the metabolism, the N-acylated fatty (amid) acid is only contained as a fatty acid composition of the ceramide itself and corresponding glycosyl derivatives, and is cleaved off during the metabolism of secondary messengers.

The specific acylation of the molecule determines the potency of gangliosides/ceramides and their metabolites as signal-mediating molecules. The metabolism of ganglioside derivatives by substrate-specific enzymes (sphingomyelinase, ceramidase, sphingosinacyl transferase) and the enzymatic regulation of the ceramide activity as a signal molecule (ceramide hydrogenase, ceramide kinase) is co-determined by the acyl pattern as a structural element. In addition, saturated fatty acids having a carbon length of up to C24 cause rapid ganglioside metabolism (de novo synthesis/conversion). The specific acylation of the molecule is also relevant for the influence of gangliosides on various intracellular regulatory enzymes (phosphokinase C, phospholipase D and various protein phosphatases/kinases).

Hitherto known biological functions of gangliosides are:

Development of the gastrointestinal tract of newborn babies; development of the intestinal immunosystem, cf. Rueda, R., Maldonado, J., Narbona, E., Gil, A. Early human Development 1998, 53, p 135-147; Jensen, R. Lipids 1999, 34, 1243-1271.

Anti-carcinogenic effects (induces apoptosis, stops cell growth), cf. Vesper, H., Schmelz, E.-M., Nikolova-Karakashian, M. N., Dillehay, D. L., Lynch, D. V., Merril, A. H. Jr. J. Nutr. 1999, 129, 1239-1250; Farooqui, A., Harrocks, L. A., Farooqui, T., Chemistry and Physics 2000, 106, 1-29.

T-cell differentiation is induced (induction of the cell maturation); inhibition of T-cell response, cf. Yanagihava, K., Kato, E., Hitomi, S., Sunamoto, J., Wada, H. Glycoconjugate J. 1999, 16, 59-65.

Prostaglandin synthesis and COX gene expression is enhanced, cf. Wu, G., Lu, Z., Ledeen, R. W. Glycoconjugate J. 1996, 13, 235-239.

The biological functions of gangliosides extensively described in literature are mainly associated with the composition of the oligosaccharide chain. On the other hand, less functional importance is attached to the lipid portion, although it is known that the bio-activity of gangliosides is co-determined by the fatty acid composition.

Most previously existing patents therefore deal mainly with the oligosaccharide chain, or do not indicate a specification for the fatty acids, cf. JP 92105616. Others only state the proportion of saturated to unsaturated fatty acids, cf. JP 3101691.

U.S. Pat. No. 5,366,963 22/94 describes the correlation between the fatty acid portion and a chain length of <C18 and >C20 and the immunosuppressive action of a ganglioside mixture, the fatty acids C18 and C20 being explicitly excluded.

It has now surprisingly been found that the lipid component in gangliosides has a much greater importance than was previously assumed.

It is therefore the object of the present invention to provide a ganglioside mixture with an improved biological activity.

This object is achieved by the teaching of the claims.

The gangliosides in this case correspond to the following general formula I:

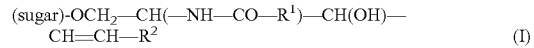

$$(\text{sugar})\text{-OCH}_2\text{---CH(---NH---CO---R}^1\text{)---CH(OH)---} \\ \text{CH==CH---R}^2 \quad (I)$$

This general formula I describes in a formulaic way those gangliosides which represent the basis for the inventive mixture. We are not concerned here with the provision of these types of gangliosides as such, for the inventive mixture may even consist entirely of known gangliosides. Rather, the invention consists of the fact that, of the gangliosides comprised by the above formula and the residues defined in the present documents and comprised by this general formula, the group —CO—R1 is made up of certain fatty acids in certain amounts. General formula I hence provides the computational and material reference base to which the data relating to materials and quantities given herein refer. It is, for example, possible to obtain inventive mixtures solely by re-mixing already known gangliosides or ganglioside mixtures.

Of course, modifications etc. of the gangliosides may also be carried out, which will be explained in more detail below.

The residue $R^2$ in this case signifies a straight, saturated alkyl residue or a straight alkenyl residue, with both of the residues possessing 10 or more C-atoms, e.g. up to 30 C-atoms. The residue $R^2$ can thus have 10, 11, 12, 13, 14, 15, 16, 17, 18, 19, 20, 21, 22, 23, 24, 25, 26, 27, 28, 29 and 30 C-atoms. Preferably, the number of C-atoms is even, e.g. 14, 16 and 18. The alkenyl residue may have one, two or three double bond(s).

The residue $R^1$ signifies a straight, saturated alkyl residue with 10 or more C-atoms, e.g. up to 30 C-atoms. The residue $R^1$ may thus have 10, 11, 12, 13, 14, 15, 16, 17, 18, 19, 20, 21, 22, 23, 24, 25, 26, 27, 28, 29 and 30 C-atoms. Preferably, the number of C-atoms is even, e.g. 18, 20, 22 and 24. The residue $R^1$ together with the keto group bound thereto represents a fatty acid, which is bound to the residues of the molecule in the form of an amide. This residue —CO—$R^1$ is designated as acyl-fatty acids in the present documents.

An essential aspect of the present invention is that in the inventive ganglioside mixture, the C20:0 fatty acid makes up at least 10 wt.-% of the acyl fatty acids (and thus of the group —CO—$R^1$, see above). This information thus concerns only one of the nonpolar aliphatic chains of the gangliosides. This means that there is no information given as to the other nonpolar aliphatic chain and the sugar unit. This other aliphatic chain may be of a known and/or any desired nature.

C20:0 designates, according to the usual nomenclature, an acyl group with 20 C-atoms (counting the carbon atom of the CO-group) without double bond (:0).

According to a preferred embodiment, the C20:0 fatty acid amounts to 10 to 15 wt.-%. With this range indication, all intermediate values, all narrower ranges, and in particular all integer intermediate values are comprised and disclosed, e.g. 11, 12, 13 and 14 wt.-%.

According to a preferred embodiment, the weight ratio of the C18:0 acyl fatty acid in the —CO—$R^1$-group to the C20:0 acyl fatty acid in the —CO—$R^1$-group is 1.0 to 3.0. Also this range indication comprises all intermediate values, all narrower ranges, and in particular single values such as 1.1, 1.2, 1.3, 1.4, 1.5, 1.6, 1.7, 1.8, 1.9, 2.0, 2.1, 2.2, 2.3, 2.4, 2.5, 2.6, 2.7, 2.8 and 2.9.

According to a further aspect of the invention, the ganglioside mixture is characterized in that the group —CO—$R^1$ may represent a C23:0 fatty acid, which makes up 10 wt.-% or less of the acyl fatty acids in the lipid portion of the ganglioside molecule.

The inventive ganglioside mixture may be animal-based (the term 'animal' used herein does not denote a human being nor a source of human origin) and/or vegetable-based lipid extracts obtained solely from fungi and monocellular organisms and/or synthetically produced gangliosides. In order to achieve the inventive composition of the acyl fatty acids, the gangliosides from the lipid extracts given above may be modified. In addition, it is possible to add isolates of gangliosides with an enriched fatty acid specification to such lipid extracts. It is also possible to add chemically synthesized gangliosides to such lipid extracts. Furthermore, the gangliosides making up the mixture may be prepared completely synthetically. It is also possible to combine different types of modifications and/or preparations. Preferably, however, it is assumed that native gangliosides are used. These may then be modified. Preferably, the inventive mixtures are thus made from native unmodified gangliosides which had been mixed with gangliosides obtained from native gangliosides and then modified. Some of the modification possibilities are given below:

Acyl chain specification of native/isolated gangliosides/ceramides by enzymatically cleaving off the N-acyl residue (sphingolipid/ceramide N-deacylase EC 351-) and new specific fatty acid esterification by acid/alkaline catalyzed chemical esterification or specific fatty acid derivatization according to Anand, J. K., Sadozai, K. K., Hakomori, S., Lipids 1996, 31, 995-998, by means of free fatty acids.

Interesterification of gangliosides by ceramide N-deacylase EC351 with specific free fatty acids, methyl esters, ethyl esters or triglycerides at an optimized pH value and temperature.

Acyl chain specification of native, isolated gangliosides/ceramides by deacylation to lysogangliosides according to Gasa, S., Kamio, K., Makita, A. J., Lipid Res. 1992, 33, 1079-1084, followed by an acid/alkaline catalyzed chemical esterification of specific fatty acids by means of free fatty acids, methyl esters, ethyl esters or triglycerides.

These modification possibilities will be discussed in more detail in the examples below.

By modifying the acyl fatty acids in terms of the invention, the biological activity of the gangliosides may be enhanced. This enhancement of the biological activity applies to the most diverse ganglioside functions. If a ganglioside has, for example, a certain biological activity, by changing or modifying the lipid portion, without changing, for example, the sugar unit, the corresponding, already existing biological activity will be enhanced. This is based on the fact that due to the inventive modification of the ganglioside lipid portion, an improved mobility of the molecule within the membranes is achieved. The high mobility and the spatial arrangement of gangliosides within the membrane (clustering, cholesterol/glycolipids micro-domains) induced by the inventive fatty acid composition lead to an enhancement of the receptor-mediated signals (influences cell surface receptors), the activity of ion channels (e.g., Na/K ATPase) and the activity of membrane-inherent enzymes (e.g. phosphokinase C), cf. Zeller, C. B., Marchase, R. B., Am. J. Physiol. 1992, 262, C1341-C1355.

Due to the modification of the lipid portion (or more precisely, of the acyl fatty acids), the already existing biological activity of gangliosides may be enhanced.

The inventive ganglioside mixture may be used in pure form, as well as in the form of an emulsion, in particular an aqueous emulsion. The ganglioside mixture may also be used together with other lipids, it being assumed that the further lipids do not influence the biological activity of the ganglioside mixture or of the gangliosides constituting this mixture. This means that the biological activity of the gangliosides is only influenced by the fatty acids present in the lipid component of the ganglioside but not by the fatty acids used in addition.

The inventive ganglioside mixture may be added to any usual foodstuff, and also to a pharmaceutical, if appropriate. In other words, the subject-matter of the invention also includes food, dietetic and pharmaceutical compositions containing an inventive ganglioside mixture.

These compositions include in particular instant food, food supplements and formulation food. In this context, a formula food is understood to mean food that has been formulated on the basis of animal (but not human) and vegetable starting materials or products. The inventive ganglioside mixture may, for example, be added as admixtures or additives to the following products, although this enumeration is not limited: milk and milk products, infant formulae and babyfood, chocolate bars, yoghurt drinks, restorative food, probe food, infusions and products for pregnant women.

The inventive ganglioside mixture may also be administered in the form of a pharmaceutical composition alone or together with one or several additional active agent(s). These may, for example, be formulated as a tablet/capsule. For the formulation of such pharmaceuticals, usual adjuvants, carriers, auxiliary agents, diluents, moisturizing agents, thickening agents, flavoring agents, sweetening agents, etc. may be used.

The pharmaceutical compositions may be administered in any usual way (e.g. parenterally or enterally) to a patient (i.e. human and animal). However, for the sake of convenience, they will be compositions suited for oral or lingual administration and formulated to suit the kind of administration.

In order to find out whether a mixture containing gangliosides or a composition containing gangliosides of the kind described here contains an inventive ganglioside mixture, it is only necessary to determine the amount of ganglioside belonging to general formula I, and then to analyze whether the specifications given here with regard to the acyl group —CO—$R^1$ are met.

If compounds or gangliosides are present that do not fall under general formula I, what is altogether possible, then these are not taken into account in the calculation.

The foods, dietetic compositions and pharmaceutical compositions containing the inventive ganglioside mixture, may be used, among other things, for improving the development of the gastrointestinal tract, the intestinal immunosystem and the neuronal system, and the treatment of destructive changes of the intestinal tract, the intestinal immunosystem and the neuronal system. All age groups, ranging from new born babies up to elderly people, may be mentioned as target groups for the inventive ganglioside mixture.

The invention will be explained in more detail below by means of examples, examples 1 to 4 describing methods of producing or modifying the inventive gangliosides or ganglioside mixtures, whereas the examples 5 to 8 explain application examples or formulation examples for the inventive compositions. The gangliosides of the inventive ganglioside mixture are known compounds or may be produced according to known methods.

EXAMPLE 1

Extraction and Separation Starting from Raw Materials

Glycosphingolipids are extracted from natural matrices (egg, soybean, animal milk, colostrum, buttermilk, animal tissues, etc.) according to Ladisch and Gillard (Ladisch S., Gillard, B., A solvent partition method for morcoscale ganglioside purification, 1984, Analytical Biochemistry 146, 220-231) with chloroform-methanol, and are purified by partitioning with diisopropyl ether-1-butanol aqueous NaCl-solution. Separation of the individual ganglioside species having a different saccharide composition may be performed using a normal phase HPLC according to Gazzotti (Gazzotti, G., Sonnino, S., Ghidoni, R., Normal phase high performance liquid chromatographic separation of non-derivatized ganglioside mixtures, 1985, J. Chromatogr. 348, 371-78). Separation and fractionation of gangliosides with regard to the acyl chain specificity is carried out by RP-HPLC as follows: gangliosides dissolved in water are fractionated by means of an RP-8 column with a solvent system of acetonitrile with 5 mM of a sodium phosphate buffer, pH 7.0. The chromatogram is recorded by UV/VIS detection (wavelength: 195 nm) according to Wagener (Wagener, R., Kobbe, B., Stoffel, W., Quantification of gangliosides by microbore high performance liquid chromatography, 1996, J. Lipid Res. 37, 1823-1829) or by a light scattering detection according to Caboni, (Caboni, M. F., Menofta, S., Lercker, G., Separation of phospholipids in different foods with light-scattering detector, 1996, JAOCS 73, 1561-1566). The obtained fractions are quantified by a five-point calibration of the chromatogram. The individual acyl chain specificities are accumulated by means of an automatic fraction collector, and may be recomposed according to a mixing ratio of the acyl chain specification.

EXAMPLE 2

Enzymatic Transesterification

Glycosphingolipids are subjected to a transesterification with specific free fatty acids either directly in the natural matrix (egg, soybean, animal milk, colostrum, buttermilk, animal tissue, etc.) or after extraction according to Ladisch and Gillard (Ladisch S., Gillard, B., A solvent partition method for morcoscale ganglioside purification, 1984, Analytical Biochemistry 146, 220-231). Transesterification of the substrate takes place by means of a substrate-specific ceramide-N-deacylase E.C.3.5.1.—(Sigma-Aldrich, Inc., USA) with specific free fatty acids at optimal pH values in 0.1% Triton X100 (N-acyl chain hydrolysis at a pH of 5.0-6.0; condensation of the lysosphingolipid with free fatty acids at pH 7.0) (Ito, M., Kurita, T., Kita, K., A novel enzyme that cleaves the N-acyl linkage of ceramides in various glycosphingolipids as well as sphingomyelines to produce their lyso-forms, 1995, J. Biol. Chem. 270, 24370-24374; Kita, K., Okino, N., Ito, M., Reverse hydrolysis reaction of a recombinant alkaline ceramidase of Pseudomonas aeruginosa, 2000, Biochim. Biophys. Acta 1485 (2-3), 111-120). The modified glycpsphingolipids may either be used directly in a mixing ratio of the acyl chain specification, or may be recomposed with other components according to a mixing ratio of the acyl chain specification.

EXAMPLE 3

Chemical Fatty Acid Modification

Glycosphingolipids are extracted from natural matrices (egg, soybean, animal milk, colostrum, buttermilk, animal tissue, etc.) according to Ladisch and Gillard (Ladisch S., Gillard, B., A solvent partition method for morcoscale ganglioside purification, 1984, Analytical Biochemistry 146, 220-231) and are purified (see above). In order to change the acyl chain specification of isolated gangliosides, the extract is converted according to Gasa, S. (Gasa, S., Kamio, K., Makita, A., Improved preparation method for Isogangliosides, 1992, J. Lipid Res. 33, 1079-1084) by N-trifluoroacetylation of the sphingosine, followed by an N-acetylation and subsequent mild saponification into corresponding dideacylated gangliosides (protective group). These are chemically deacylated into lysogangliosides. The cleavage of the acyl chains from native gangliosides may also be performed through a direct chemical hydrolysis according to Gaver and Sweeley (Gaver, R. C., Sweeley, C. C., Methods for methanolysis of sphingolipids and direct determination of long chain bases by gas chromatography, 1995, J. Lipid Res. 24, 1389-1397) or by an acidic hydrolysis according to Andu (Kadowaki, H., Bremer, E. G., Evans, J. E., Jungalwala, F. B., McCluer, R H, Acetonitrile-hydrochloric acid hydrolysis of gangliosides for high performance liquid chromatographic analysis of their long chain bases, J. Lipid Res. 1983, 24, 1389-1397) by means of incubation of the substrate with 0.5M HCl in acetonitrile (or methanol) and 4M $H_2O$ at 75° C. for 2 hours. The resulting lysogangliosides are separated from the free fatty acids, salts and low-molecular contaminants through anion exchange chromatography by means of aminopropyl phase. The new acyl chain specificity of the lysogangliosides with specific free fatty acids, methyl esters or ethyl esters is obtained by an acid/alkaline catalyzed chemical esterification. It is likewise possible to specifically acylate the resulting glycosphingolipids chemically with specific fatty acids according to Anand (Anand, J. K., Sadozai K. K., Hakomori, S., A simple method for the synthesis of ceramides and radiolabeled analogues, 1996, Lipids 31, 995-998). Using diethyl phosphoryl cyanide in combination with triethylamine, the sphingolipid amines are coupled with specific fatty acids. In this way it is possible to obtain specific N-fatty acid sphingolipids, cerebrosides and gangliosides. The reaction is free of racemates. The desired products are obtained in a yield of 85-90%. The advantage of this method is that the specifically esterified gangliosides are present in a highly pure form. The modified glycosphingolipids may be recomposed with other components according to a mixing ratio of the acyl chain specification.

EXAMPLE 4

Chemical Synthesis

Glycosphingolipids are chemically or chemo-enzymatically synthesized with specific fatty acids through a total chemical synthesis according to Duclos (Duclos, R. I., The total synthesis of ganglioside GM3, 2000, Carbohydr. Res. 328, 489-507). The glycosphingolipids produced synthetically in a pure form having a defined fatty acid specificity may be recomposed with other components according to a mixing ratio of the acyl chain specification.

EXAMPLE 5

Preparation of Baby Formulations/Infant Formulae

For providing glycosphingolipids for the preparation of baby formulations, dried buttermilk material is used. The fatty acid distribution of ganglioside extracts from buttermilk having a fat distribution of the N-acyl-fatty acids of C18:0 (10-20 wt.-%) and C20:0 (0.01-0.5 wt.-%) based on the total amount of the N-acyl-fatty acids is adjusted by mixing in a ratio of 1:6 with a raw material (see below) modified in its fatty acid distribution and having a fat distribution of the N-acyl-fatty acids of C18:0 (6-9 wt.-%) and C20:0 (60-90 wt.-%) to a new N-acyl fatty acid distribution of C18:0 of 1-3 wt.-% and C20:0 of 10-15 wt.-%. The raw material modified in its fatty acid distribution of glycosphingolipids, based on 100 g of solid matter content of a formulation food, is prepared as follows: The glycosphingolipids, mainly GM1, GM3, GD1a, GD1b from buttermilk (Uelzena, Germany) having a fat portion of 10-15%, are extracted and purified according to Ladisch and Gillard (Ladisch S., Gillard, B., A solvent partition method for morcoscale ganglioside purification, 1984, Analytical Biochemistry 146, 220-231). 10 g of dried buttermilk material (corresponds approximately to 1 liter of milk) are mixed with 50 ml of methanol and 50 ml of chloroform, extracted for 15 minutes, and subsequently pelletized at 4° C. The supernatant is evaporated to about ¼ of its original volume by rotary evaporation or lyophilization.

Subsequently, the protein portions of the solution are precipitated at −20° C. and pelletized. The supernatant is evaporated until dryness. For partitioning, the extract is resuspended with 60 ml of diisopropyl ether/1-butanol (v/v) 60:40, and subsequently added to 30 ml of water. A phase separation takes place. The aqueous phase contains the glycosphingolipid portion (about 1 g/l) of the raw material. The fatty acid modification is performed as follows: 1 g of glycosphingolipid extract (about 0.83 mmol at MG 1200) is suspended in 10 ml of 20 mM sodium phosphate solution with 0.1% of Triton X100, 100 U ceramide-N-deacylase is added and incubated at 37° C. for 1-2 hours. The hydrolysis of the N-acyl-fatty acids takes place at pH 5-6. Subsequently, the solution is adjusted to an end concentration of 25 mM sodium phosphate by addition of sodium phosphate. The specific free fatty acid is added in a molar ratio of 1:10 to the glycosphingolipid used (8.3 mmol C20:0). The transesterification takes place at 37° C. at pH 7-8 over 1-2 hours. The modified glycosphingolipids are purified through a preparative chromatography (RPC18), the conditioning of the phase taking place with chloroform/methanol/0.1M KCl solution (v/v/v) 3:98:74. The reaction solution is applied to the column. The column is washed with chloroform/methanol/0.1M KCl solution (v/v/v) 3:98:74, water and methanol/water (v/v) 1:1. The ensuing elution of the glycosphingolipids is carried out with ethanol and chloroform/methanol (v/v) 2:1. The eluate obtained is evaporated until dryness. This process yields approximately 0.8 g of glycosphingolipids per liter of buttermilk having a fat distribution of the N-acyl-fatty acids of C18:0 (6-9 wt.-%) and C20:0 (60-90 wt.-%) based on the total amount of the N-acyl-fatty acids.

A protein-adapted infant milk formula (Aptamil® from Milupa) containing 11.8 g of protein, 56.9 g of carbohydrates, 24.9 g of fat, 2.5 g of minerals and vitamins and 45 mg of taurine is prepared in the usual manner in the form of a bead product. The ganglioside mixture described in a) is added in an amount of 0.2-500 mg/100 mg based on the solid matter content of the formula food.

EXAMPLE 6

Food Supplements

Ganglioside extracts from bovine colostrum, egg lecithin or buttermilk were adjusted by modification of the N-acyl-fatty acid distribution or by mixing a raw material with a raw material (see above) modified in its fatty acid distribution having a fat distribution of the N-acyl-fatty acids to give a fatty acid distribution of 1-3 wt.-% C18:0 and 10-15 wt.-% C20:0 based on the total amount of the N-acyl-fatty acids.

The described ganglioside mixture is formulated in softgel capsules with 10 to 50 mg/capsule.

EXAMPLE 7

A Product for Pregnant Women

An effervescent tablet (final weight 4.15 g) (Neovin® from Milupa) is prepared in a manner known per se by admixing 10 to 50 mg of the described ganglioside mixture. One tablet per day is dissolved in 150 ml water and swallowed.

EXAMPLE 8

A Product for the Elderly and Debilitated Persons

A balanced pulverized restorative food (Dilsana® from Milupa) containing 22.5 g of protein, 7.7 g of fat, 60.8 g of carbohydrates, 5.4 g of minerals and vitamins is prepared in a manner known per se by incorporating 0.2-500 mg of the described ganglioside mixture based on 100 mg of the solid matter content of the formula food. Up to 3×50 g per day of the food are dissolved in 150 ml water and administered.

The invention claimed is:

1. A Dietetic, pharmaceutical or food composition containing a mixture of gangliosides of the formula I:

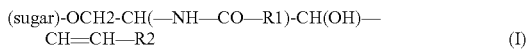
(sugar)-OCH2-CH(—NH—CO—R1)-CH(OH)—CH=CH—R2    (I)

wherein
(sugar) represents a sugar residue,
the group —CO—R1 represents an acyl fatty acid bound to the residue of the molecule in the form of an amide,
R1 represents a straight, saturated alkyl residue having at least 10 C-atoms,
R2 represents a straight, saturated alkyl residue having at least 10 C-atoms or a straight alkenyl residue having at least 10 C-atoms and one, two or three double bond(s), wherein in the gangliosides of formula I present in said mixture, at least 10 wt.-% of the group —CO—R1 and thus of the acyl-fatty acids are a C20:0 fatty acid, and
the composition is incorporated in an instant food, a food supplement or a formulation food.

2. The composition according to claim 1, wherein the C20:0 fatty acid makes up 10 to 15 wt.-% of the group —CO—R1 and thus of the acyl-fatty acids.

3. The composition according to claim 1, wherein the group —CO—R1 includes a C18:0 fatty acid and a C20:0 fatty acid, and the weight ratio of said C18:0 fatty acid to the C20:0 fatty acid of the group —CO—R1 in said mixture is 1.0 to 3.0.

4. The composition according to claim 1, wherein the group —CO—R1 includes a C23:0 fatty acid, which makes up 10 wt.-% or less of the acyl fatty acids in the lipid portion of the ganglioside molecules.

5. The composition according to claim 1, wherein the ganglioside mixture is composed of unmodified gangliosides obtained from naturally existing sources of animal and/or vegetable origin.

6. The composition according to claim 1, wherein the ganglioside mixture is composed of modified gangliosides obtained from naturally existing sources of animal and/or vegetable origin.

7. The composition according to claim 1, which is formulated as an aqueous emulsion.

8. The composition according to claim 1, which is a component of a fat blend.

9. A Dietetic, pharmaceutical or food composition containing a mixture of gangliosides of the formula I:

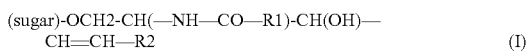
(sugar)-OCH2-CH(—NH—CO—R1)-CH(OH)—CH=CH—R2    (I)

wherein
(sugar) represents a sugar residue,
the group —CO—R1 represents an acyl fatty acid bound to the residue of the molecule in the form of an amide,
R1 represents a straight, saturated alkyl residue having at least 10 C-atoms,
R2 represents a straight, saturated alkyl residue having at least 10 C-atoms or a straight alkenyl residue having at least 10 C-atoms and one, two or three double bond(s), wherein in the gangliosides of formula I present in said mixture,
the group —CO—R1 includes a C23:0 fatty acid, which makes up 10 wt.-% or less of the acyl fatty acids in the lipid portion of the ganglioside molecules; and
the group —CO—R1 further includes a C20:0 fatty acid, which makes up 10 to 15 wt.-% of the acyl fatty acids.

10. The composition according to claim 9, wherein the group —CO—R1 includes a C18:0 fatty acid and a C20:0 fatty acid, and the weight ratio of said C18:0 fatty acid to the C20:0 fatty acid of the group —CO—R1 in said mixture is 1.0 to 3.0.

11. The composition according to claim 9, wherein the ganglioside mixture is composed of unmodified gangliosides obtained from naturally existing sources of animal and/or vegetable origin.

12. The composition according to claim 9, wherein the ganglioside mixture is composed of modified gangliosides obtained from naturally existing sources of animal and/or vegetable origin.

13. The composition according to claim 9, which is formulated as an aqueous emulsion.

14. The composition according to claim 9, which is a component of a fat blend.

15. The composition according to claim 9, wherein the composition is incorporated in an instant food, a food supplement or a formulation food.

16. A Dietetic, pharmaceutical or food composition containing a mixture of gangliosides of the formula I:

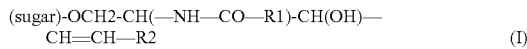
(sugar)-OCH2-CH(—NH—CO—R1)-CH(OH)—CH=CH—R2    (I)

wherein
(sugar) represents a sugar residue,
the group —CO—R1 represents an acyl fatty acid bound to the residue of the molecule in the form of an amide,
R1 represents a straight, saturated alkyl residue having at least 10 C-atoms,
R2 represents a straight, saturated alkyl residue having at least 10 C-atoms or a straight alkenyl residue having at least 10 C-atoms and one, two or three double bond(s), wherein in the gangliosides of formula I present in said mixture, at least 10 wt.-% of the group —CO—R1 and thus of the acyl-fatty acids are a C20:0 fatty acid,
the group —CO—R1 includes a C23:0 fatty acid, which makes up 10 wt.-% or less of the acyl fatty acids in the lipid portion of the ganglioside molecules, and
the group —CO—R1 includes a C18:0 fatty acid and a C20:0 fatty acid, and the weight ratio of said C18:0 fatty acid to the C20:0 fatty acid of the group —CO—R1 in said mixture is 1.0 to 3.0.

17. The composition according to claim 16, wherein the C20:0 fatty acid makes up 10 to 15 wt.-% of the group —CO—R1 and thus of the acyl-fatty acids.

18. The composition according to claim 16, wherein the ganglioside mixture is composed of unmodified gangliosides obtained from naturally existing sources of animal and/or vegetable origin.

19. The composition according to claim 16, wherein the ganglioside mixture is composed of modified gangliosides obtained from naturally existing sources of animal and/or vegetable origin.

20. The composition according to claim 16, which is formulated as an aqueous emulsion.

21. The composition according to claim 16, which is a component of a fat blend.

22. The composition according to claim 16, wherein the composition is incorporated in an instant food, a food supplement or a formulation food.

* * * * *